(12) United States Patent
Shibata et al.

(10) Patent No.: US 8,416,292 B2
(45) Date of Patent: Apr. 9, 2013

(54) DEFECT INSPECTION APPARATUS AND METHOD

(75) Inventors: Yukihiro Shibata, Fujisawa (JP); Yasuhiro Yoshitake, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1012 days.

(21) Appl. No.: 12/389,962

(22) Filed: Feb. 20, 2009

(65) Prior Publication Data

US 2009/0213215 A1    Aug. 27, 2009

(30) Foreign Application Priority Data

Feb. 20, 2008 (JP) .................... 2008-038172

(51) Int. Cl.
*H04N 7/18* (2006.01)
(52) U.S. Cl. .......................... 348/92; 356/337
(58) Field of Classification Search .............. 348/86, 348/92; 356/336, 337
See application file for complete search history.

(56) References Cited

U.S. PATENT DOCUMENTS

| 6,654,110 B2 * | 11/2003 | Yonezawa et al. ......... 356/237.2 |
| 7,508,526 B2 * | 3/2009 | Ogawa et al. ................ 356/491 |
| 2008/0174780 A1 * | 7/2008 | Kreh ............................ 356/402 |

FOREIGN PATENT DOCUMENTS

| JP | 10-221267 | 8/1998 |
| JP | 2000-216208 | 8/2000 |
| WO | WO 99/06823 | 2/1999 |

* cited by examiner

*Primary Examiner* — Viet Vu
(74) *Attorney, Agent, or Firm* — Antonelli, Terry, Stout & Kraus, LLP.

(57) ABSTRACT

In a defect inspection apparatus for inspecting a wafer provided with a circuit pattern for defects, the illuminating direction of illuminating light rays is selectively determined such that an area containing a defect that scatters light of high intensity coincides with the aperture of a dark-field detecting system, and such that regularly reflected light regularly reflected by a pattern, which is noise to defect detection, does not coincide with the aperture of the dark field detecting system.

14 Claims, 8 Drawing Sheets

DEFECT INSPECTION APPARATUS AND METHOD

BACKGROUND

The present invention relates to a defect inspection method of inspecting a minute pattern formed on a substrate by a thin-film forming process, such as a semiconductor device fabricating process or a flat panel display manufacturing process, for defects formed in the pattern and contaminants adhering to the pattern, and a defect inspection apparatus for carrying out the same.

A semiconductor device inspecting apparatus is disclosed in Int. Pat. Pub. No. WO99/06823. This known semiconductor device inspecting apparatus focuses a radiation beam fallen on a surface of a wafer at an incident angle in a line on the surface of the wafer. Light scattered by an illuminated linear area is received by an optical detector, and an image sensor forms a scattered image. A central part of the image sensor is a flat surface substantially perpendicular to the surface on which the flat illuminating beam falls. Thus, scattered light received by the image sensor is lateral scattered light. The image formed by the image sensor is compared with an image of an adjacent die on which the same pattern is formed, to determine whether or not the pattern is defective.

Wafers subjected to inspection are provided with various patterns, respectively, and various kinds of defects are formed by various causes. The size of defects has been progressively diminished with the progressive miniaturization of patterns formed by semiconductor device fabricating processes. Generally, the quantity of scattered light is proportional to the sixth power of particle size. Therefore, the quantity of scattered light from defects decreases as the defects are miniaturized. When a dark field detection system is used, an image of a pattern is brighter than those of defects if a scattering cross section of the pattern is greater than defects. Therefore, the intensity of illuminating light is adjusted so that the brightness of an image of the pattern may not saturate the image sensor. In such a case, detection of defects through image processing is difficult because the brightness of images of defects in the image of the pattern is low. If the intensity of illuminating light is increased such that the brightness of the image of the pattern is higher than the saturation level of the image sensor to form images of defects in high brightness, it is difficult to detect the defects on the pattern because brightness of the image of the pattern is higher than the saturation level of the image sensor.

An image suitable for high-sensitivity inspection can be obtained by forming the image of the pattern in a moderate brightness to enhance the brightness of the images of the defects relatively. The technique mentioned in Int. Pat. Pub. No. WO99/06823 focuses a flat beam in a bright line on the surface of a wafer to illuminate a linear area in the surface of the wafer. In this state, reflected light from a part extending in a direction perpendicular to the length of the illuminating line of the pattern is distributed in a width corresponding to the NA (numerical aperture) of focused illumination on a Fourier transform plane formed by an objective lens. When the reflected light from the pattern is filtered by a spatial filter, the aperture of the objective lens is limited, and hence, the resolution of the objective is deteriorated.

The technique mentioned in Int. Pat. Pub. No. WO99/06823 uses an oblique detecting system having an optical axis inclined at an angle to a normal direction to the surface of the wafer. When the angle between the normal direction to the surface of the wafer and the optical axis of the oblique detecting system and the NA of the illuminating light are in some relationship, an optical system can be disposed so that the reflected light from a part extending in a direction perpendicular to the length of the illuminating line of the pattern is not detected. When the NA of the oblique detecting system is increased to improve the resolution, i.e., to increase the intensity of scattered light from small defects, the NA cannot be increased because the wafer interferes mechanically with the objective.

SUMMARY

Accordingly, the present invention provides a defect inspection method capable of inspecting an entire surface of a wafer in a high sensitivity for defects, and a defect inspection apparatus for carrying out the defect inspection method.

According to the present invention, the direction of illuminating light can be selectively determined such that an area in which the intensity of scattered light scattered by defects is high coincides with an aperture of a dark field detecting system, and light regularly reflected by a pattern, which is noise to defect detection, does not coincide with the aperture of the dark field detecting system.

Representative (non-limiting) examples of the present invention will be briefly described below.

(1) The present invention provides a defect inspection method of inspecting a specimen having a circuit pattern for defects including the steps of: projecting first illuminating light rays on the specimen from the direction of a first main pattern included in the circuit pattern, and detecting first scattered light scattered by an illuminated first area to form a first digital image of the first scattered light; projecting second illuminating light rays on the specimen from the direction of a second main pattern included in the circuit pattern, and detecting second scattered light scattered by an illuminated second area to form a digital image of the second scattered light; and determining presumable (i.e., candidate) defects by comparing the first and the second digital image.

(2) The present invention provides a defect inspection apparatus for inspecting a specimen provided with a circuit pattern for defects including: a first illuminating optical system for projecting first light rays on the specimen from the direction of a first main pattern included in the circuit pattern; a second illuminating optical system for projecting second light rays on the specimen from the direction of a second main pattern included in the circuit pattern; a first optical detection system disposed above the specimen to detect first scattered light flux scattered by a first area illuminated with the first light rays; a second optical detection system disposed above the specimen to detect second scattered light flux scattered by a second area illuminated with the second light rays; and an image processing unit for comparing a first digital image formed by the first optical detection system and a second digital image formed by the second optical detection system to determine presumable (i.e., candidate) defects.

(3) The present invention provides a defect inspection apparatus for inspecting a specimen provided with a circuit pattern for defects including: a first illuminating optical system for projecting first illuminating light rays on the specimen from the direction of a first main pattern included in the circuit pattern; a second illuminating optical system for projecting second illuminating light rays on the specimen from the direction of a second main pattern included in the circuit pattern; an optical detection system disposed above the specimen to detect first scattered light flux scattered by a first area illuminated with the first illuminating light rays and second scattered light flux scattered by a second area illuminated with the second illuminating light rays; and an image processing unit for comparing a first digital image formed by the first scattered light flux and a second digital image formed by the second scattered light flux, to determined presumable (i.e., candidate) defects.

These features and advantages of the invention will be apparent from the following more particular description of preferred embodiments of the invention, as illustrated in the accompanying drawings.

BRIEF DESCRIPTION OF THE DRAWINGS

FIGS. 2A1, 2B and 2C1 are views assisting in explaining a scatter distribution when a wafer is illuminated from a Y-direction by the example defect inspection apparatus of the present invention;

FIGS. 2A2, and 2C2 are views assisting in explaining a scatter distribution when a disadvantaged defect inspection apparatus is used;

DETAILED DESCRIPTION

Example embodiments of the present invention will be described.

First Embodiment

Figure 1:
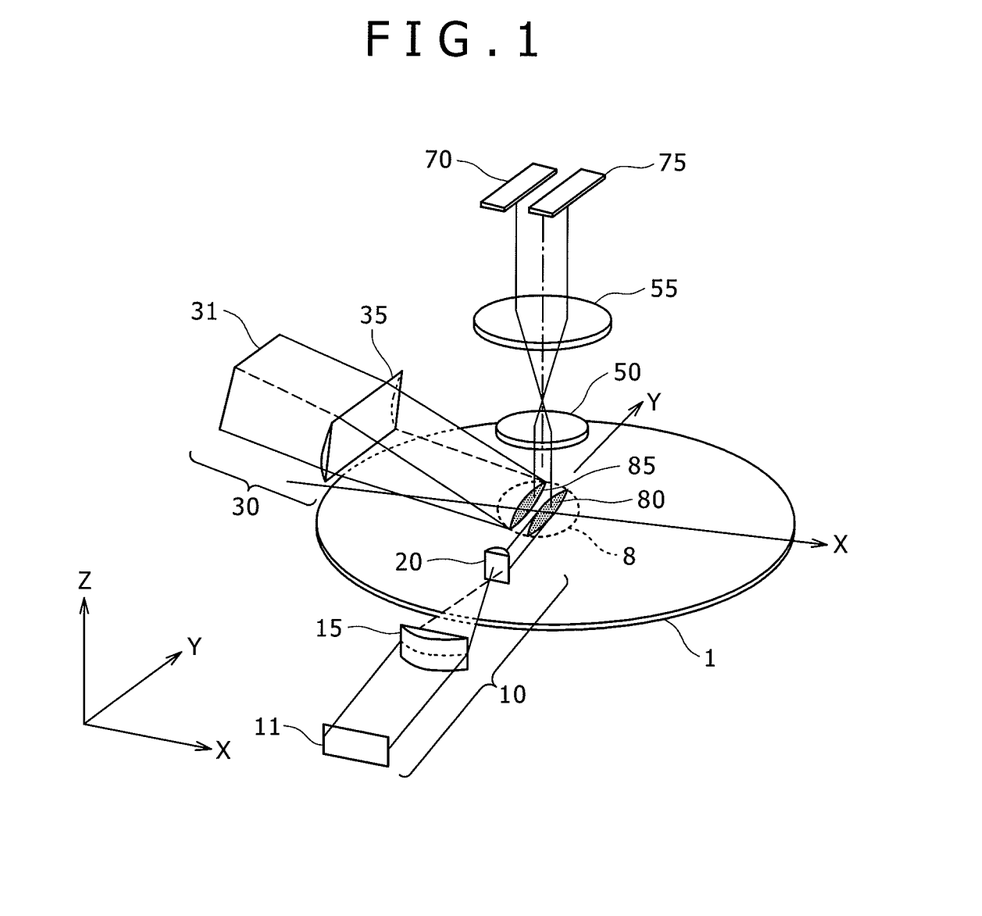
FIG. 1 is a schematic perspective view of an example optical system included in an example optical defect inspection apparatus according to the present invention.

FIG. 1 shows an example optical system included in an example optical defect inspection apparatus according to the present invention, in a schematic perspective view. Suppose that a circuit pattern is formed in an X-direction and a Y-direction. An illuminating system includes a Y-direction illuminating system 10 and an X-direction illuminating system 30. The Y-direction illuminating system 10 projects a shaped, oblique light beam 11 inclined to a normal to the surface of a wafer 1 from a direction parallel to the pattern through a cylindrical lenses 15 and 20 in a direction parallel to the wafer 1, to illuminate area 80. The oblique light beam is not focused on the surface of the wafer 1. The X-direction illuminating system 30 is disposed such that a light beam is projected from the X-direction at a position on the wafer 1 separated from an illuminated area on the wafer 1 illuminated by the Y-direction illuminating light beam. A light beam 31 incident on a cylindrical lens 35 included in the X-direction illuminating system 30 is gathered in the direction of an angle of elevation (in a direction of an angle from the surface of the wafer to the light beam) so as to illuminate a linear area 85 on the surface of the wafer 1.

Suppose that the wafer 1 is moved continuously in the X-direction to form an image. Then, the respective lengths of the illuminated linear areas 80 and 85 illuminated respectively by the Y-direction illuminating system 10 and the X-direction illuminating system 30 are substantially parallel to the Y-direction. Both the illuminated linear areas 80 and 85 are in the visual field 8 of an objective lens 50 disposed with its optical axis extended parallel to a normal to the surface of the wafer 1. Light propagating in the NA of the objective lens 50 among the light reflected and scattered by the illuminated linear area 80 parallel to the Y-direction, falls on the objective lens 50, and is then focused by an imaging lens 55 to form a scattered image of the light passed through the objective 50 and imaging 55 lenses onto an image sensor 70.

Desirably, the NA of the objective lens 50 may be 0.7 or above. Similarly, light propagating in the NA of the objective lens 50 from among the light reflected and scattered by the illuminated linear area 85 and parallel to the X-direction, falls on the objective lens 50 and is focused by an imaging lens 55 to form a scattered image of the light passed through the objective lens 50, onto an image sensor 75. The images of the scattered light scattered by the illuminated linear areas 80 and 85 illuminated from the Y- and the X-direction, are formed separately on the image sensors 70 and 75, respectively.

Since, it is supposed (for discussion purposes) that main patterns formed on the wafer 1 are in the X- and the Y-direction, the patterns are illuminated from the X- and the Y-direction parallel to the patterns. For example, when the pattern is a wiring line extending at 45° to the X-direction, the pattern is illuminated from a direction at 45° to the X-direction. Thus, only a first illuminating system for illuminating from the direction of a first main pattern and a second illuminating system for illuminating from the direction of a second main pattern are needed.

Figure 2A:
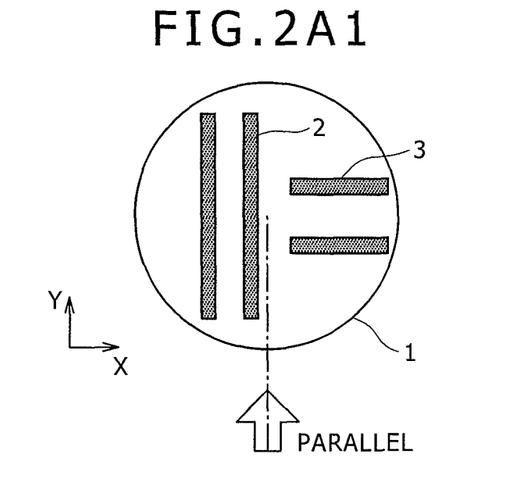
Figure 2A:
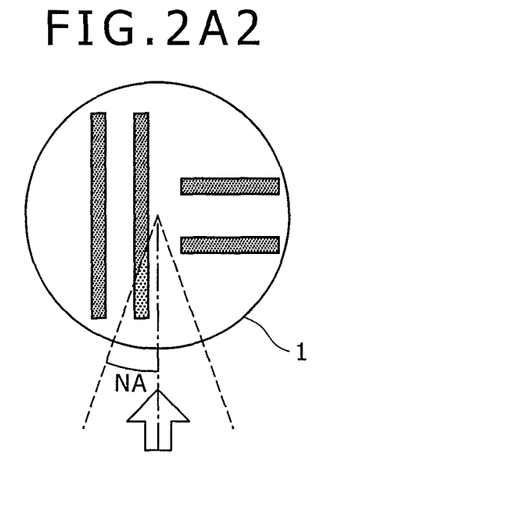
Figure 2B:
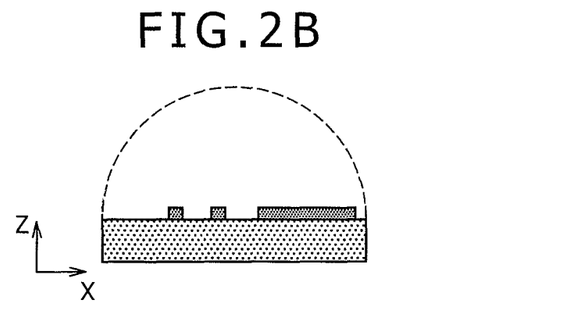

FIGS. 2A1, 2B and 2C1 show example illuminated areas on the wafer 1, illuminated by Y-direction illumination. For example, FIG. 2A1 shows an illuminated area illuminated in a direction parallel to the Y-direction in an XY-plane. Suppose that a Y-direction pattern 2, namely, a first main pattern, and an X-direction pattern 3, namely, a second main pattern, are formed on the wafer 1. FIG. 2B is an example sectional view in an XZ-plane.

Figure 2C:
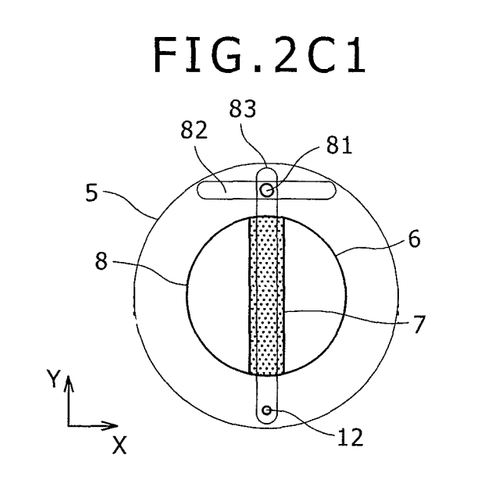
Figure 2C:
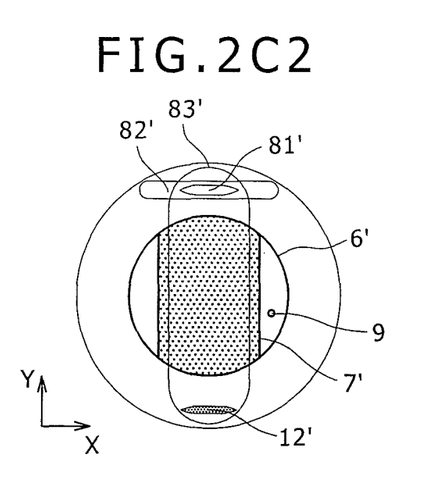

Suppose that an imaginary hemisphere is placed on the wafer 1 to represent scattered light rays scattered in all directions by the wafer 1. FIG. 2C1 shows an example of the scattered light rays fallen on the imaginary hemisphere on an XY-plane. Light rays propagated parallel to the surface of the wafer 1 reach a circle 5 formed by the imaginary hemisphere on the XY-plane. Light rays scattered in a direction parallel to the normal to the surface of the wafer 1 reach the center of the circle 5. Regularly reflected light ($0^{th}$-order light) reaches a position 81 axisymmetric with illuminating light 12 fallen in this area with respect to the center axis of the circle 5. Light rays regularly reflected by, and scattered by, the Y-direction pattern, pass the position of the regularly reflected light rays, and reach an area 82 perpendicular to the direction of the pattern. Light rays regularly reflected by, and scattered by, the X-direction pattern, pass the position of the regularly reflected light rays, and reach an area 83 perpendicular to the direction of the pattern.

For example, suppose that an area surrounded by a circle 8 corresponds to the visual field of the objective lens 50. Then, the area 82 where the light reflected by, and scattered by, the pattern parallel to the illuminating direction Y, is outside the circle 8, i.e., outside the NA of the objective lens 50. Therefore, an image of the pattern is not formed, and the light scattered by the X-direction pattern perpendicular to the illuminating direction Y are detected. Therefore, the effect of the light scattered by the X-direction pattern can be reduced by using a spatial filter 6 (for example, comparable in size to the circle 8) having a shading part 7 corresponding to the position where the light scattered by the X-direction pattern reaches. In FIG. 2C1, the spatial filter 6 and the visual field defined by the circle 8 are superposed.

FIG. 2A2 is an example view assisting in explaining a disadvantageous semiconductor device inspecting apparatus. (FIG. 2A2 may be somewhat similar to an arrangement mentioned in Int. Pat. Pub. No. WO99/06823, but in no way represents an admission of prior art, i.e., see actual published references for actual prior art). As shown in FIG. 2A2, a direction in which lines are extended is the same as an illuminating direction Y. The surface of a wafer 1 is illuminated linearly by setting the NA in the direction of the width of the lines.

FIG. 2C2 shows an example distribution of scattered light when the surface of the wafer 1 is so illuminated. Since the NA is set in the direction of the width of the lines, an illuminating light beam 12' and a regularly reflected light beam 81' expand in the X-direction, an area 82' where light scattered by a Y-direction pattern parallel to the illuminating direction Y is substantially the same as the area 82 shown in FIG. 2C1, and an area 83' where light scattered by an X-direction pattern reaches is wider than the area 83 shown in FIG. 2C1. Therefore, a spatial filter 6' for filtering the light scattered by the X-direction pattern needs a wide shading part 7' and the aperture 9 of the objective lens 50 is narrow. Consequently, the resolution of the semiconductor device inspecting apparatus mentioned in disadvantageous arrangements, such as in Int. Pat. Pub. No. WO99/06823, is deteriorated, and the same apparatus cannot efficiently capture scattered light from defects and detecting sensitivity is unsatisfactory. The invention of the present disclosure, instead has an embodiment which uses parallel light rays for linear illumination of a wafer 1 and Y-direction illumination parallel to the length, to prevent the deterioration of resolution.

In FIG. 2C1, light from the X-direction pattern is filtered by the spatial filter 6. The scattered light scattered by the X-direction pattern distributes in a wide range and cannot be perfectly stopped, and some part of the scattered light is detected. Therefore, when the wafer 1 is illuminated from the Y-direction, only an image of the X-direction pattern is formed, and an image of the Y-direction pattern is not formed.

Defects in the vicinity of the X-direction pattern are difficult to detect due to the variation and saturation of the image of the X-direction pattern. It may be possible to detect the defects in the vicinity of the X-direction pattern by illuminating the wafer 1 X-direction illumination, so that an image not including an image of the X-direction pattern parallel to the direction from which the wafer 1 is illuminated, may be formed as shown in FIGS. 3A-C.

Figure 3A:
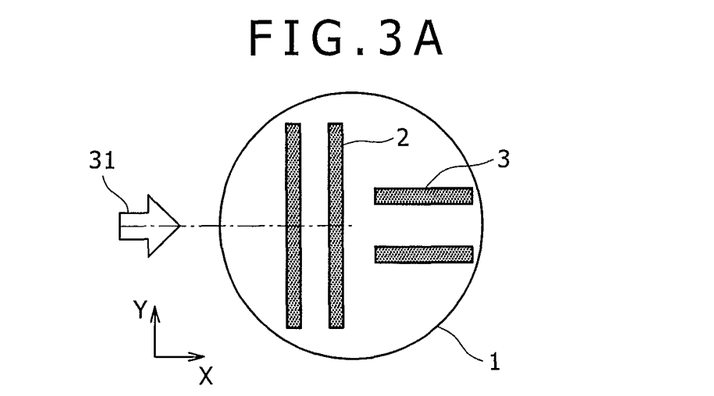
FIGS. 3A, 3B and 3C are views assisting in explaining a scatter distribution when a wafer is illuminated from an X-direction by the example defect inspection apparatus of the present invention.
Figure 3B:
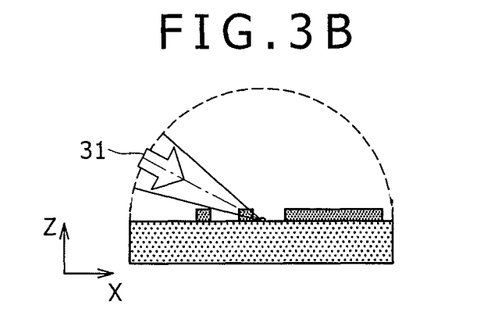
Figure 3C:
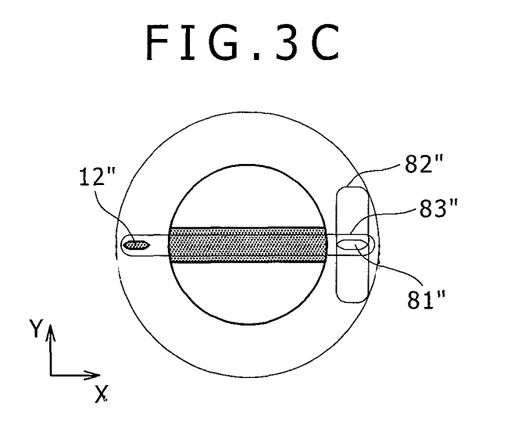

Although X-direction illumination may be parallel illumination, a narrow, linear illuminated area can be formed on the wafer by condensing a light beam for X-direction illumination because the width of an area 81" where light regularly reflected by, and scattered by, the Y-direction pattern reaches, is narrow as shown in FIG. 3C (when condensed illumination has a NA in the direction of an angle of elevation). Isolated defects not in the vicinity of the pattern can be comparatively easily detected as compared with the defects in the vicinity of the pattern, because any image of the pattern is formed near the isolated defects in an image obtained by either of the X- and the Y-direction illumination.

Either of an image formed by X-direction illumination and an image formed by Y-direction illumination does not include an image of patterns in main directions (the X- and the Y-direction pattern are spaced apart from each other on the wafer), and hence images of defects can be formed in a high S/N ratio and the sensitivity of defect detection can be improved.

Figure 8A:
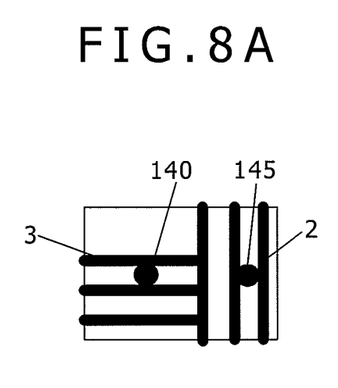
FIGS. 8A, 8B and 8C are conceptional views of example images formed by an example defect inspection apparatus according to the present invention.
Figure 8B:
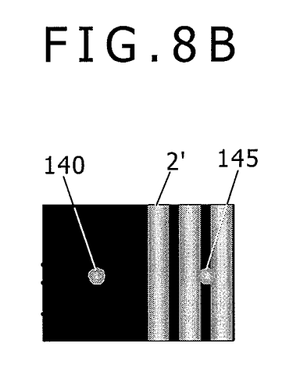
Figure 8C:
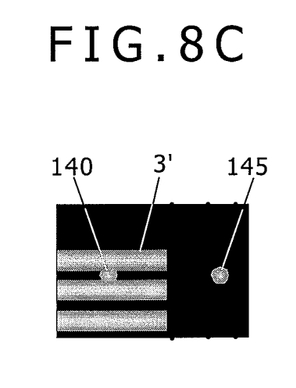

In FIGS. 2 and 3, the shading part 7 extends in a direction perpendicular to the illuminating direction. Even if the constitution does not include this, defects can be detected without using a saturating of the pattern. For example, suppose that a wafer is provided with an X-direction pattern 3 and a Y-direction pattern 2, and has defects 140 and 145 in the X-direction pattern 3 and the Y-direction pattern 2, respectively, as shown in FIG. 8A. The X-direction pattern 3 and the Y-direction pattern 2 are spaced apart from each other on the wafer. Therefore, the X-direction pattern is in a substantially not inspected area from which any information about defects is not obtained even if an image of the X-direction pattern formed by Y-direction illumination is saturated as shown in FIG. 8B, and it is possible to prevent the detection of the X-direction pattern 3 by X-direction illumination as shown in FIG. 3C.

Thus, the X- and the Y-direction pattern can be eliminated from either of the images and defects in the vicinity of the pattern can be detected from the image from which the X- and the Y-direction pattern have been eliminated, provided that the X- and the Y-direction pattern are spaced apart from each other on the wafer. Thus, even if an image of the pattern is saturated in one of the images, the image of the pattern in the other image can be suppressed and hence defects can be detected in those images. When the defect is very small as compared with the pattern, the quantity of light scattered by the pattern is large Even if the image of the pattern is saturated, the defect can be found in the other image. Therefore, the intensity of illuminating light can be adjusted so that a signal provided by the small defect can be detected, and the defect can be detected without being affected by the saturation of the image of the pattern.

Second Embodiment

Figure 4:
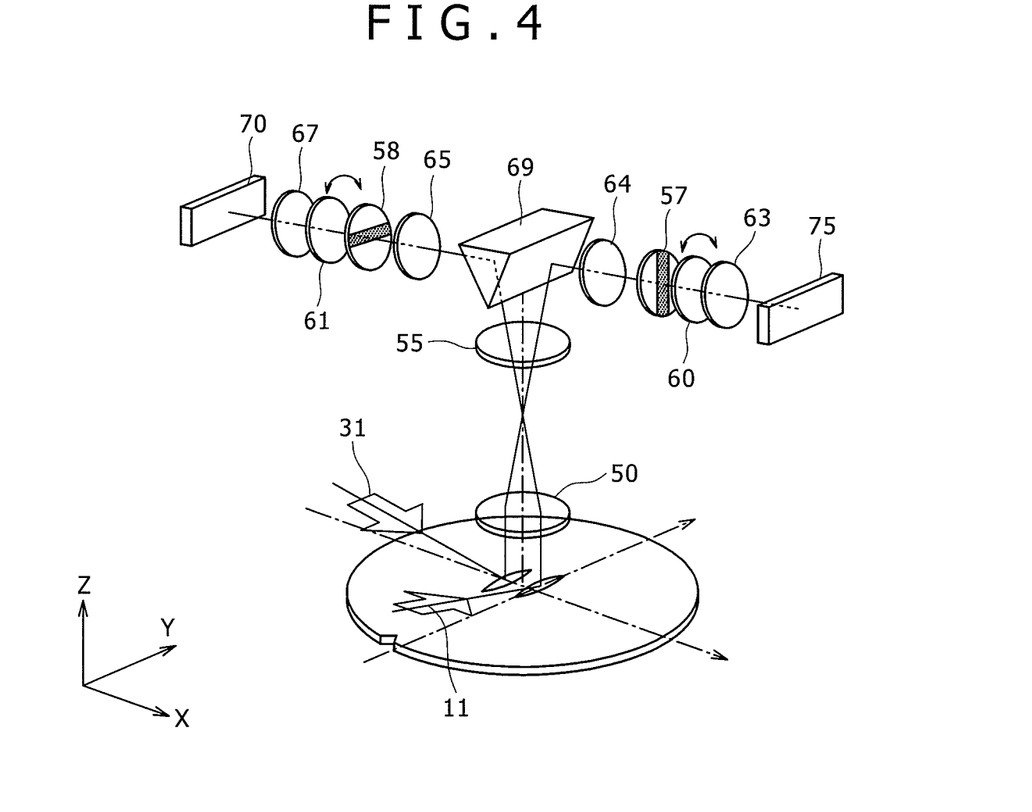
FIG. 4 is a schematic perspective view of an example detection system included in the example defect inspection apparatus of the present invention.

FIG. 4 shows an example optical system in an expansion of the example optical system shown in FIG. 1. Directions of X- and Y-direction illumination and the constitution including an objective lens 50 are the same as the first embodiment. A mirror 69 is disposed at a position on the image side of the objective lens 50 and an imaging lens 55 to separate a flux of Illuminating light 11 from the Y-direction and a flux of illuminating light 31 from the X-direction reflected and scattered by an illuminated area, so as to travel along different optical paths, respectively. Items 64 and 65 form Fourier transform planes for the two light fluxes separated by the mirror 69. Spatial filters 57 and 58 are placed in the Fourier transform planes, respectively. Rotatable polarizers 60 and 61 are used to detect specific polarized light components. Imaging lenses 63 and 67 form images of scattered light scattered by the wafer 1 on image sensors 70 and 75, respectively.

In this example embodiment, the scattered and reflected light fluxes are separated into the two light fluxes by the mirror 69, and are detected individually by the image sensors 70 and 75. Any other system may be used, provided that the scattered and reflected light fluxes can be separated into two light fluxes.

Third Embodiment

Figure 5:
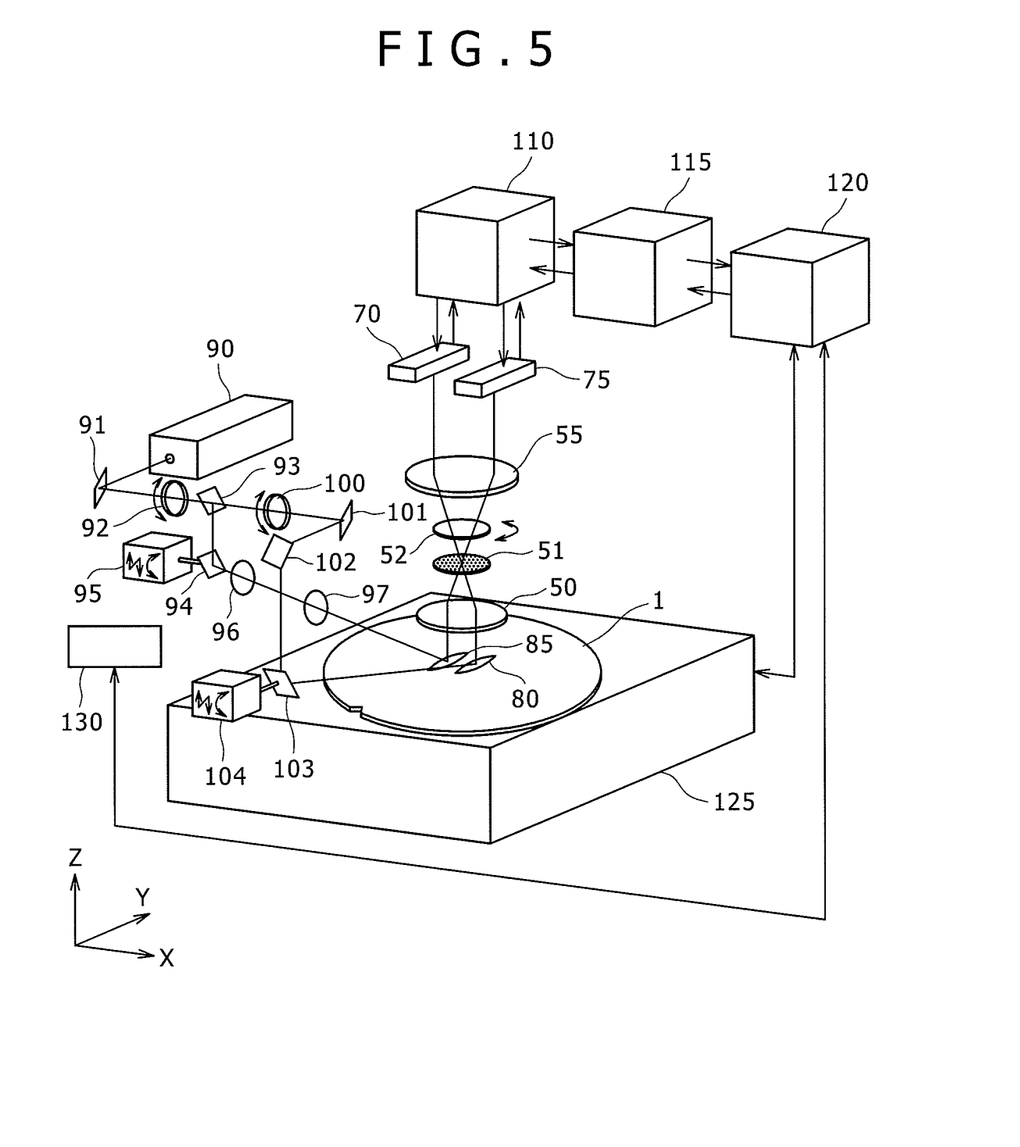
FIG. 5 is a schematic perspective view of an example defect inspection apparatus in a first example embodiment according to the present invention.

FIG. 5 shows an example defect inspection apparatus in an example third embodiment according to the present invention. A light source for illumination is a laser or a lamp. Illuminating light may be light having a wavelength in a wavelength band including deep ultraviolet radiation (DUV radiation) and visible light. The third embodiment employs a laser 90 as a light source for illumination. Parallel light rays emitted by the laser 90 are deflected by a mirror 91. The polarization of the light rays can be adjusted by a turnable wave plate 92 including a half-wave plate and a quarter-wave plate. Light rays passed through a beam splitter 93 are Y-direction illuminating light rays. The polarization of the Y-direction illuminating light rays is adjusted by a turnable wave plate 100 including a half-wave plate and a quarter-wave plate. The light rays passed through the wave plate 100 are deflected by mirrors 101 and 102 and by a mirror 103, so that the parallel light rays illuminate a linear area 80 on a wafer 1. The mirror 103 can be moved in the Z-direction and can be turned so as to change the angle of elevation of the illuminating light rays by a turning mechanism 104.

Similarly, the light rays reflected by the beam splitter 93 is the X-direction illuminating light rays. The X-direction illuminating light rays are reflected by a mirror 94 and are gathered by cylindrical lenses 96 and 97 so as to illuminate an illuminated area 85 extending in the direction of the length of a line on the wafer 1 from the direction of an angle of elevation. The mirror 97 can be moved in the Z-direction, and can be turned so as to change the angle of elevation of the illuminating light rays by a turning mechanism 95.

Light rays scattered by the wafer 1 are captured by the objective lens 50. A spatial filter 51 filters light rays diffracted by a periodic pattern. A polarizer 52 passes a specific polarized component of the light rays passed through the spatial filter 51. An imaging lens 55 forms images of the wafer 1 on image sensors 70 and 75, respectively.

Images formed by the image sensors 70 and 75 are sent to an image processing unit 110. Patterns of the same design regularly formed on the wafer 1 are compared to decide whether or not any defects are found. Results of decision and images of defects found on the wafer 1 are given to an operating unit 115 to display a map of results of inspection and images of the defects. The operating unit 115 controls operations of the defect inspection apparatus including operations for creating recipes, trial inspection, inspection and reviewing detected defects, and gives instructions to mechanical units.

That is, the operating unit 115 gives operation instructions to be given to the mechanical units to a mechanical system controller 120. The mechanical system controller 120 controls an XYZθ stage 125 and mechanical units 130 (only one of them is shown) of the optical system. The mechanical system controller 120 receives position information from a scale included in the XYZθ stage 125, and sends the position information to the image processing unit 110. The position information is used for registering the images formed by the image sensors 70 and 75 to determine whether or not the defects in the images are the same defect and to classify defects shown in the images. Images not greatly distorted can be obtained by synchronizing the image sensors 70 and 75 with the stage, even if the velocity of the stage is irregular.

The X-direction illuminated area and the Y-direction illuminated area are spatially separated from each other on the wafer 1, and images of scattered light rays from the two different directions of illumination are obtained simultaneously in the same space.

Fourth Embodiment

Figure 6:
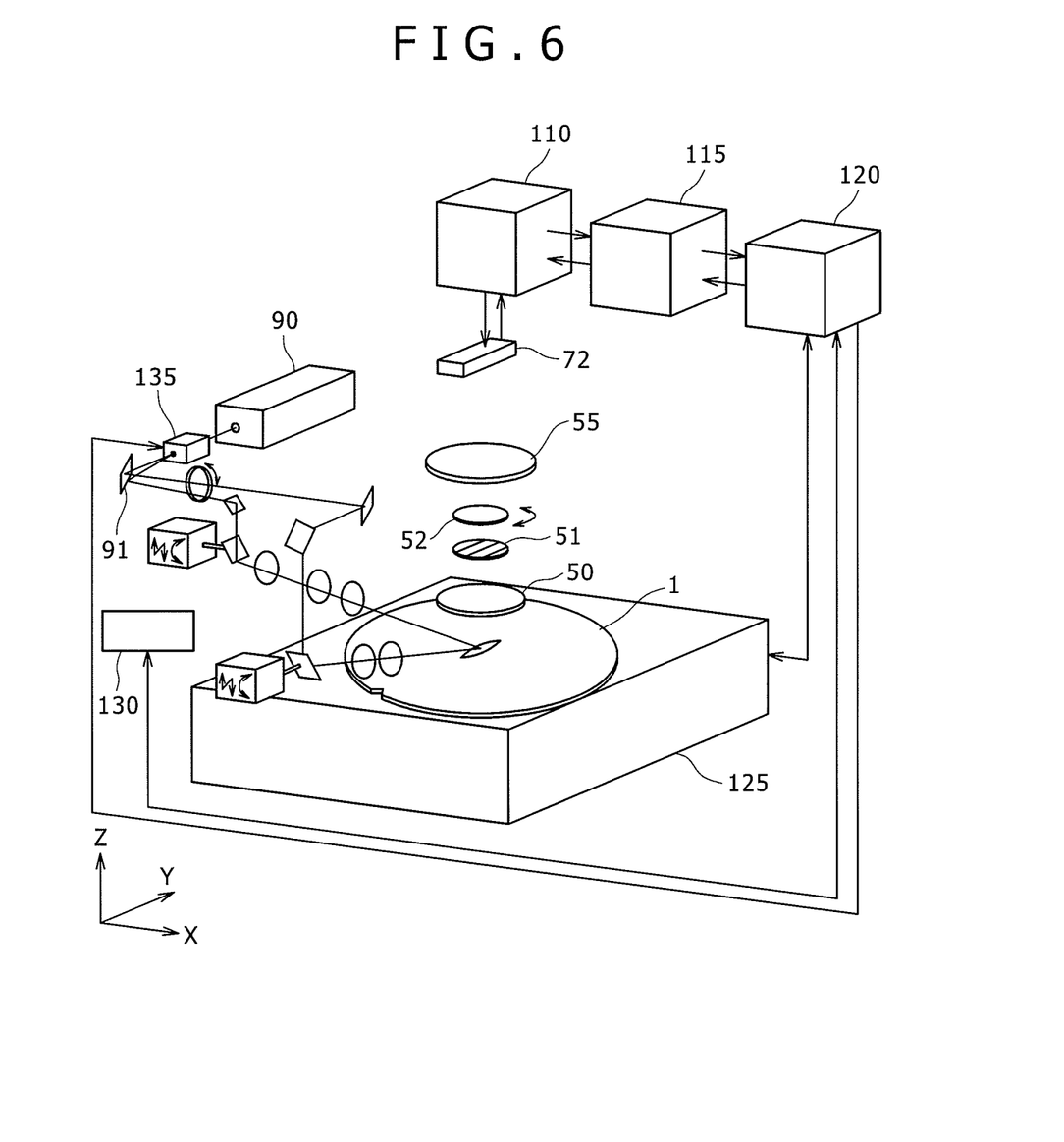
FIG. 6 is a schematic perspective view of an example defect inspection apparatus in a second example embodiment according to the present invention.

FIG. 6 shows an example defect inspection apparatus capable of simultaneously forming images of scattered light rays from two different illumination directions in the same space. Since the basic configuration of the defect inspection apparatus shown in FIG. 6 is the same as the defect inspection apparatus shown in FIG. 5, only parts of the defect inspection apparatus shown in FIG. 6 different from those of the defect inspection apparatus shown in FIG. 5, will be described.

The defect inspection apparatus shown in FIG. 6 differs from that shown in FIG. 5 in that an opto-acoustic module 135 receives parallel light rays emitted by a laser 90, and rapidly changes the optical axis of an outgoing light beam, so as to alternate Y-direction illumination and X-direction illuminate rapidly. Since detection is executed in a time-division detection mode, only a single image sensor 72 is needed.

Figure 7:
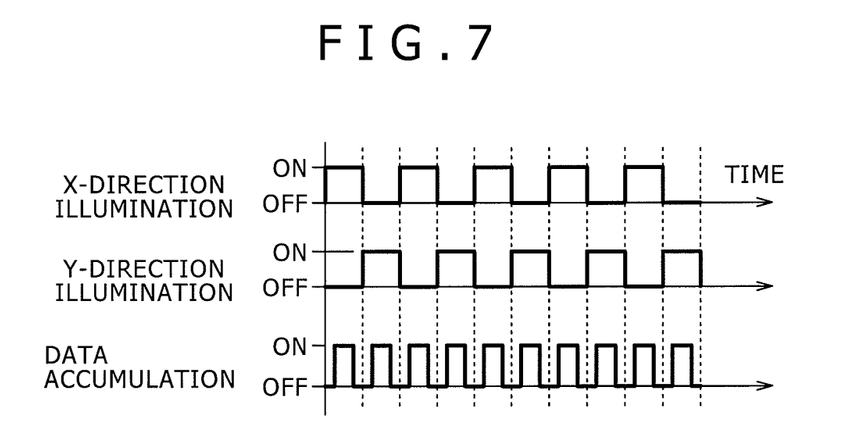
FIG. 7 is a diagram assisting in explaining an example time-division detecting method to be carried out by an example defect inspection apparatus according to the present invention.

FIG. 7 shows the timing of an example changing of the illuminating direction by the opto-acoustic module 135, and data accumulating operation of the image sensor 72. The line rate, namely, the reciprocal of accumulation time of the image sensor 72, is, for example, twice the period of alternating X-direction illumination and Y-direction illumination. Oversampling is performed at twice the moving speed of an image in an image plane to form an image under X-direction and an image under Y-direction illumination alternately.

An image processing unit 110 edits two images, respectively, under the X-direction illumination and Y-direction illumination from those images, and compares the edited images. Thus, images of scattered light rays from different illuminating directions in the same space can be obtained simultaneously in a time-division mode. Although the defect inspection apparatus that operates in a time-division detection mode is shown in FIG. 6, various changes may be made therein without departing from the gist of the present invention.

Fifth Embodiment

Figure 9:
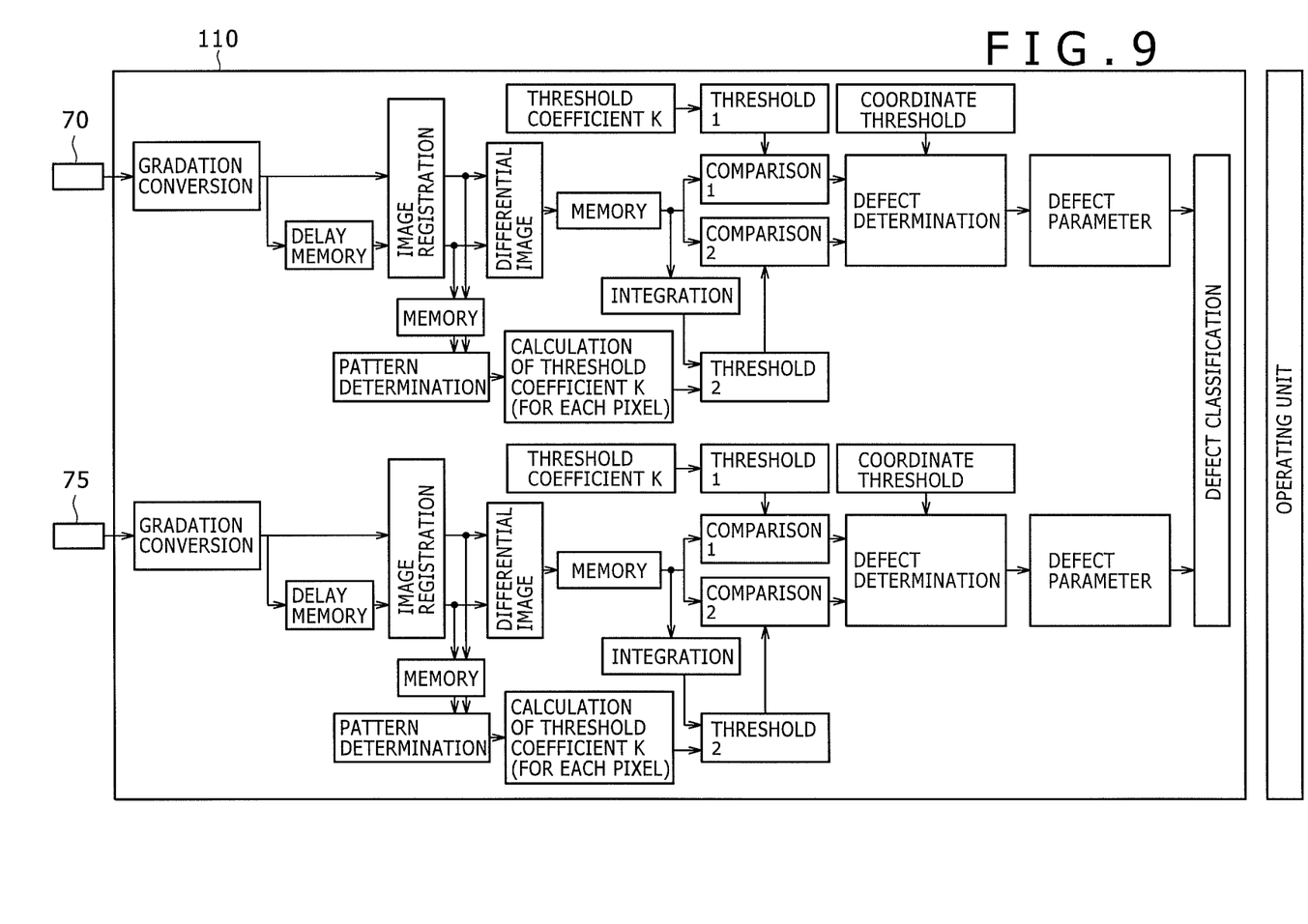
FIG. 9 is a block diagram assisting in explaining an example image processing procedure to be carried out by an example defect inspection apparatus according to the present invention.

FIG. 9 shows an example image processing procedure for processing a plurality of images formed by the plurality of image sensors by each of the foregoing embodiments. An example defect detecting procedure for detecting defects in the images formed by the image sensors 70 and 75 of the two detection systems is shown. The brightness resolution of images formed by the first image sensor 70 and the second image sensor 75, have, for example, 1024 brightness gradation levels. The images are subjected to gradation conversion to convert the images into those, for example, of 256 gradation levels. The brightness conversion characteristic for gradation conversion may be linear or nonlinear.

An example image processing procedure for processing the image formed by the first image sensor 70 will be described. The image is processed by gradation conversion to obtain an image having, for example, 256 brightness gradation levels. The image thus obtained, is given to a registering unit and a delay memory. The image sent to the delay memory is sent to the registering unit with a delay time corresponding, for example, to the pitch of a pattern of the same design formed on a die. Thus, the image obtained in a real-time detection mode and the image of the adjacent die, are sent to the registering unit, and the two images are registered. Then, a differential image is calculated by using the registered images.

The differential image is subjected to two threshold processes. A first threshold processing system processes the absolute value of the differential image by a fixed value. Values of image parameters, such as brightness and size, in an area above this threshold are sent to a defect deciding unit. A second threshold processing system determines brightness irregularity and such from a plurality of differential images, produces a threshold based on the brightness irregularity, namely, dispersion threshold, and compares the differential image with the threshold. This threshold may be, for example, a floating threshold. A second threshold processing system, similarly to the first threshold processing system, sends the values of image parameters in an area above the floating threshold to the defect deciding unit.

Overall decision of defects is made on the basis of those values of image parameters received from the two threshold processing systems. Some special patterns may have a large brightness irregularity and normal parts in such a pattern are decided mistakenly to be defects in some cases. High possibility of occurrence of erroneous decision in detecting defects in specific patterns is used. Coordinate information about a wafer is given to the defect deciding unit, values of image parameters in an area in which erroneous decision is liable to occur are not decided to be defects even if those values are above the threshold or a flag indicating high possibility of erroneous decision is set, and is sent to the next image parameter calculating unit. The image parameter calculating unit uses the image formed by the image sensor for calculating values of image parameters more minutely than the values of image parameters given to the comparing unit.

The image formed by the second image sensor 75 is processed similarly, and values of image parameters of defects are calculated.

The calculated values of image parameters of the images formed by the first image sensor 70 and the second image sensor 75, are used for classifying defects. Results of classification, the coordinate information and the values of parameters of images are given to an operating unit. The operator can visually recognize the output information. Those pieces of information are given to a host system managing LSI manufacturing processes.

The constitution, functions and the contents of image processing described above in connection with the foregoing example embodiments, can be used in various combinations without departing from the scope of the present invention. Each of the foregoing example embodiments is provided with the two illuminating optical systems to deal with the two circuit patterns respectively extending in the two directions, the defect inspection apparatus may be provided with three or more illuminating optical systems when the defect inspection apparatus is required to deal with circuit patterns respectively extending in three or more directions.

The present invention can suppress reflected light reflected by a normal pattern and acting as a noise source. Therefore, it is possible to reduce an area that cannot be substantially inspected due to the saturation of the pattern image resulting from the variation of the brightness of the pattern image of the normal pattern. Thus, the defect inspection apparatus and the defect inspection method of the present invention can inspect the entire surface of a wafer for defects at high sensitivity.

The invention claimed is:

1. A defect inspection method of inspecting a specimen provided with a pattern for defects, said defect inspection method comprising:
projecting first illuminating light rays on a first region of the specimen from a direction of a first main pattern included in the pattern, and detecting first scattered light scattered by an illuminated first area, to form a digital image of the first scattered light;
projecting second illuminating light rays on a second region of the specimen different from the first region from a direction of a second main pattern included in the pattern, and detecting second scattered light scattered by an illuminated second area, to form a digital image of the second scattered light; and
determining presumable defects by comparing the first and the second digital image;
wherein the first illuminating light rays to the first region and the second illuminating light rays to the second region, are projected simultaneously.

2. The defect inspection method according to claim 1, wherein longitudinal axes of the illuminated first area and the illuminated second area are parallel.

3. The defect inspection method according to claim 1, wherein the first illuminating light rays are projected in a parallel illumination mode, and the second illuminating light rays are projected in a condensation illumination mode in which the second illuminating light rays are gathered in a direction of angle of elevation with respect to the specimen.

4. The defect inspection method according to claim 1, wherein the first and the second area on the specimen are also projected in substantially the same space, and the first and the second illuminating light rays are also projected for illumination in a time-division mode.

5. The defect inspection method according to claim 1, wherein directions from which the first and the second illuminating light rays are projected, respectively, on the specimen, are substantially perpendicular to each other.

6. A defect inspection method of inspecting a specimen provided with a pattern for defects, said defect inspection method comprising:
scanning the specimen in a horizontal plane;
illuminating a linear area on the specimen from a direction perpendicular to a direction in which the specimen is scanned in a parallel illumination mode, by a first illuminating system;
illuminating a linear area on the specimen from a direction parallel to the direction in which the specimen is scanned in a condensed illumination mode, by a second illuminating system;
capturing first and second scattered light rays by a detecting optical unit having a NA (numerical aperture) of 0.7 or above;
separating the scattered first illuminating light flux and the scattered second illuminating light flux captured by the detecting optical unit, so as to direct separated light to travel along two optical paths, respectively;
detecting images formed on the optical paths by image sensors disposed on the optical paths, respectively; and
determining presumable defects by comparing the images detected by the image sensors;
wherein the illuminating the linear area on the specimen from the direction perpendicular to the direction in which the specimen is scanned in the parallel illumination mode, and the illuminating the linear area on the specimen from the direction parallel to the direction in which the specimen is scanned in the condensed illumination mode, are project simultaneously.

7. The defect inspection method according to claim 6, wherein directions from which the first and the second illuminating light rays are projected, respectively, on the specimen, are substantially perpendicular to each other.

8. A defect inspection apparatus for inspecting a specimen provided with a pattern for defects, said defect inspection apparatus comprising:
- a stage configured to support a specimen thereon;
- a first illuminating optical system configured to project first illuminating light rays on the specimen from a direction of a first main pattern included in the pattern;
- a second illuminating optical system configured to project second illuminating light rays on the specimen from a direction of a second main pattern included in the circuit pattern;
- a first optical detection system disposed above the specimen, to detect first scattered light flux scattered by a first area illuminated with the first illuminating light rays;
- a second optical detection system disposed above the specimen, to detect second scattered light flux scattered by a second area illuminated with the second illuminating light rays; and
- an image processing unit configured to determine presumable defects by comparing a first digital image formed by the first optical detection system and a second digital image formed by the second optical detection system;
- wherein the first illuminating light rays on the specimen, and the second illuminating light rays on the specimen, are projected simultaneously.

9. The defect inspection apparatus according to claim 8, wherein the first and the second illuminating light rays are projected in a parallel illumination mode.

10. The defect inspection apparatus according to claim 8, wherein the first illuminating light rays are projected in a parallel illumination mode, and the second illuminating light rays are projected in a condensation illumination mode in which the second illuminating light rays are gathered in a direction of angle of elevation with respect to a specimen.

11. The defect inspection apparatus according to claim 10, wherein the second illuminating optical system includes a cylindrical lens disposed so as to gather illuminating light rays emitted by a light source in a direction of angle of elevation with respect to the specimen.

12. The defect inspection apparatus according to claim 8, wherein the first detection optical system includes a spatial filter disposed so as to filter scattered light flux scattered by the second main pattern.

13. The defect inspection apparatus according to claim 8, wherein the second optical detection system includes a spatial filter disposed so as to filter scattered light flux scattered by the first main pattern.

14. The defect inspection apparatus according to claim 8, wherein the first and the second optical detection system are provided with image sensors, respectively.

* * * * *